United States Patent [19]
Durham

[11] Patent Number: 5,657,766
[45] Date of Patent: Aug. 19, 1997

[54] HEAD AND NECK IMMOBILIZER

[76] Inventor: Donald E. Durham, 143 Cedar Forest Dr., Smyrna, Tenn. 37167

[21] Appl. No.: 553,748

[22] Filed: Oct. 23, 1995

[51] Int. Cl.$^6$ .................................................. A61F 5/37
[52] U.S. Cl. .................................................. 128/870; 5/637
[58] Field of Search .................................. 128/845, 846, 128/869, 870, 876; 5/630, 636, 637, 648, 81 R

[56] References Cited

U.S. PATENT DOCUMENTS

| | | | |
|---|---|---|---|
| 4,127,120 | 11/1978 | Appleyah | 128/870 |
| 4,259,950 | 4/1981 | Klippel | 128/870 |
| 4,589,407 | 5/1986 | Koledin | 128/869 |
| 4,979,520 | 12/1990 | Boone | 128/870 |
| 5,211,185 | 5/1993 | Garth et al. | |
| 5,265,625 | 11/1993 | Bodman | |
| 5,305,754 | 4/1994 | Honeywell et al. | 128/870 |
| 5,400,802 | 3/1995 | Niemeyer et al. | 128/870 |

OTHER PUBLICATIONS

Copies from Moore Medical Corporation product catalog #4175, p. 40, Head Immobilizers.

*Primary Examiner*—Michael A. Brown
*Attorney, Agent, or Firm*—Waddey & Patterson; Laura K. Thomas

[57] ABSTRACT

A head immobilizing apparatus comprising a main board having a central portion and spaced apart side edge portions. Positioned along the side edge portions are apertures to accommodate backboard engaging straps and head immobilizing straps. The backboard engaging straps are provided to secure the main board to a backboard in an emergency medical situation. The head immobilizing straps can be operably positioned in a variety of locations depending upon the apertures for positioning the head immobilizing straps. A pair of removable head supports are operably attached to the central portion of the main board through a hook and loop material. A head cushion is positioned at the central most portion of the main board. The main board of the head immobilizer is constructed of a high strength corrugated disposable material and the upright cushions and head pillow are constructed of an open cell foam to absorb blood and bodily fluids during trauma of the head of the patient.

12 Claims, 4 Drawing Sheets

HEAD AND NECK IMMOBILIZER

BACKGROUND OF THE INVENTION

1. Field of the Invention

The present invention relates generally to immobilizing apparatuses for the head, but more particularly to immobilizing apparatuses incorporating removable pads, a plurality of straps, and a base headboard attachable to a back board used by emergency medical personnel.

2. Description of the Related Art

The art to which the invention relates includes devices or apparatuses for immobilizing the head.

The initial treatment administered to a patient by emergency medical personnel can be critical to the future well-being of the patient. If not handled properly during the early stages of treatment, a patient may experience serious long-term or permanent effects. When it is believed that a patient may have suffered injury to the cervical spine, i.e. the neck, or may be at risk for cervical spine injury during treatment, it is critical that emergency medical personnel immobilize the patient's head during transport to prevent the exacerbation or occurrence of such injury. Typically, the patient is placed on a body board or backboard and the head is positioned in a device or apparatus to maintain the head and cervical spine in a stable position.

Many of the devices found in the prior art do not sufficiently restrict movement of the head and cervical spine and, thus, require supplemental means for achieving adequate immobilization. Furthermore, many of the devices found in the prior art are non-disposable and must be sterilized or disposed of after use to reduce exposure to the AIDS virus in accordance with the OSHA regulation regarding blood born pathogens. The sterilization of non-disposable head immobilizers, however, can be time-consuming, costly and impractical.

Other devices, while providing adequate immobilization of the head and cervical spine, do not provide adequate access to the patient's ears to permit emergency medical personnel to perform a complete diagnosis of the patient's condition. If it is believed that injury has occurred to the head or neck region, it is desirable that emergency medical personnel have access to the patient's ears to observe fluid discharge from the ear.

Several United States patents have attempted to provide an immobilizing device that meets all of these criteria. U.S. Pat. No. 5,265,625 granted to Bodman and incorporated by reference as if fully set forth herein is directed to a device for immobilizing the head comprising left and right complimentary blocks. The blocks contact the skull with skull supporting surfaces diverging outwardly and upwardly to provide a wedging action to immobilize the skull against lateral movement and to position the skull so that it aligns with the neck. The skull supporting surface surrounds but does not cover the ear.

U.S. Pat. No. 5,305,754 granted to Honeywell et al. and incorporated by reference as if fully set forth herein is directed to a head immobilization device comprising an H-shaped manufacturing blank having fold lines. When assembled, the blank forms a device having a pair of triangular cylinders which extend longitudinally upward from the top surface of a head support center section on opposite sides of such section to prevent lateral movement of the head. Ear hole slots are provided in the inner sides of the cylinders. The device is provided with adhesive tape on the bottom of the center section to attach the device to a flat surface, such as a back-board. The sides of the triangular cylinders are releasably fastened by hook and loop fasteners.

U.S. Pat. No. 5,400,802 granted to Niemeyer et at. and incorporated by reference as if fully set forth herein is directed to a head immobilizer comprising a pair of complementary blocks sized and shaped to snugly fit about opposing sides of a patient's head during transportation. Each block includes a curved portion for disposition alongside the patient's head, a neck portion for disposition adjacent the patient's neck, and an upper tapered portion to permit the neck portions to be inwardly movable with respect to each other when the head portions are adjacent the patient's head.

U.S. Pat. No. 5,211,185 directed to Garth et al. and incorporated by reference as if fully set forth herein is directed to a head immobilization device comprising a foundation portion and a restraining portion. The foundation portion comprises a foundational panel and an adhesive first spine board engaging element situated on the lower surface of the foundation panel. The restraining portion comprises a base panel, two side panels extending laterally from the outer sides of the base panel, and at least one band of material for affixing the side panels to each other in suitable conformance with the patient's head.

A device sold by Ferno Washington, Inc. under the trade designation Ferno-Model 445 Head Immobilizer comprises a pair of polyvinyl coated closed cell foam complementary blocks having side openings. The blocks are positioned on either side of the skull and are secured to a body board with a pair of straps that extend from one side of the board across the patient's forehead and chin to the other side of the board.

Until now, it is believed that a disposable head immobilizing apparatus comprising removable head cushion pads, a plurality of immobilizing straps and attachment straps, and a base headboard having a plurality of apertures for accommodating immobilizing and attachment straps, backboard handles and backboard hardware, has not been invented.

SUMMARY OF THE INVENTION

An embodiment of the present invention includes a main headboard or base component through which a plurality of apertures are formed. The apertures include a handle cut into the baseboard, a variety of spaced apart pairs of strap attachment slots and at least one pair of adjustable head immobilizing strap and slot combinations. Other optional apertures may further include cutaways to enable buckles or protruding components of an emergency backboard to protrude therethrough to enable the main board to be secured to the backboard or supplemental attachment straps to be secured to the hardware attached to the backboard to which the embodiment of the invention rests.

The preferred embodiment of the present invention also includes a central portion of the main board capable of receiving the head of a patient. The head is preferably rested upon the central portion of the main board on a head support pad or planar pillow to provide adequate cushioning of the head. Spaced apart from, and on both sides of the head support pad or pillow, and contained on the central portion of the main board, is a head pad attachment sheet. The attachment sheet is preferably formed from a hook or loop material. The hook or loop material is attached to the central portion of the main board apart from the head support pad and a pair of removable cushion components also having a hook and loop component may be operably attached thereto.

Accordingly, the preferred embodiment of the present invention also includes a pair of head cushions pads. Each head cushion pad has a bottom surface configured with the cooperating component of the hook and loop material to enable the pad to be removably attached and engaged to the main board on which the head pad attachment sheet is applied. Each head cushion has a universal configuration such that there is preferably no left or right head cushion component. In this manner, when the head cushions are removed they may simply be replaced without the need for aligning them as left or right components.

Each head cushion pad in its preferred embodiment therefore includes a bottom surface, a pair of spaced apart planar surfaces extending orthogonally from the bottom surface to form the sides of each head cushion pad, a top surface which includes an arcuate cutaway portion to enable access to the ears of the patient when the patient's head rests upon the head cushion attached to the central portion of the main board.

The top surface also includes an angled or beveled portion on either side of the arcuate ear cutout of the head cushion. The beveled surfaces enable the mobilizing straps to pass over the cushion and provide a greater surface contact between the head cushion and the immobilizing straps for an enhanced securing relationship therebetween to effectively immobilize the head of the patient. Each head cushion therefore also has a width defined by the surface existing between the spaced apart upright planar portions which are orthogonal to the bottom which in turn attaches to the head pad attachment sheet as defined above.

In an optional embodiment, a section of the head cushions may also be removed to enable better adjustment of the immobilizing straps with respect to the head cushion. The cutaway portions are formed generally in the area between the surface associated with its width and either one of the upright planar portions extending orthogonally from the bottom portion to which the entire head cushion attaches to the head pad attachment sheet. The cutaway enables the immobilizing straps to overlie each head cushion without significantly depressing the head cushion during use.

The preferred materials associated with the major components of the present invention are generally as follows: the board to which virtually all of the components are attached, or allowed to pass through its one of many pluralities of apertures, is constructed of a heavy duty, high strength, corrugated cardboard-like or plastic material. The corrugations extend axially across the preferred embodiment of the invention such that when the apertures are formed in the edge portions of the main board the corrugations run perpendicular to the length of the cutouts to provide added strength surrounding each cutout. If the corrugation were designed to run along the long axis of each aperture in the manner similar to the handle described below, the main board might have a tendency to tear or fragment in response to forces associated with the immobilizing straps or straps that attach the main board to a backboard in an emergency situation. Note, however, that while the preferred alignment of the corrugations is transverse or perpendicular to the apertures through which the immobilizing straps or tie-down straps are passed, the corrugation is parallel with the handle aperture positioned at the top of the main board. Alternatively, other suitable materials of sufficient strength and durability are contemplated to be within the scope of the present invention.

The handle aperture is simply provided as a means to grasp the main board in combination with a backboard when used in emergency situations. That is, the handle aperture is provided to concentrically overlie the handle aperture of a backboard and the handle attachment strap is simply provided as a means to ensure the concentric placement of the handle aperture of the main board of the embodiment of the present invention and the handle aperture of the backboard to which it is attached. In this manner, the handle attachment strap further prevents movement or minimizes the possibility of movement of the main board with respect to the backboard to which it is attached when it is used.

The preferred materials of the head cushions are preferably an open cell foam of a light color. A light color is preferred, as is any color other than the color red which is so closely associated with the color of blood. In this manner, the head cushions with its open cell foam are positioned on either side of the patient's head and any bleeding that might occur is preferably absorbed by the head cushions and easily seen because of the contrast in the color between the blood and the color of the head cushion material. Similarly, the color of the main board head pad attachment sheet as well as the head cushion are all preferably of a light color dissimilar to the color of blood so that the attending physician or emergency personnel can easily make a visual determination of the existence or presence of blood and the points adjacent to the patient's head from which the blood might be seeping or be flowing.

The various straps of the present invention preferably include a pair of spaced apart backboard tie-down straps. Each strap is preferably laced through a pair of spaced apart slots of the main board. That is, a slot positioned on one edge of the main board has a mating slot positioned at the opposite edge of the main board at substantially the same location with respect to a hypothetical center line along the main board. Looping the straps through the slots and passing the straps beneath the main board such that they are underneath and visible at the bottom surface of the main board enables the main board to be attached to a backboard in an emergency situation. Thus, the straps are preferably constructed of a hook and loop foam backed material for its light weight and strength as well as having tabbed ends of either the hook or looped material to enable the tabbed ends to re-engage the strap as it surrounds the backboard enabling the bottom surface of the main board to be adjacent to and in contact with the top surface of a backboard in an emergency situation. In a similar manner, it is preferred that a plurality of backboard attachment straps are provided at various locations on the man board to provide more than one source of stable contact between the main board of an embodiment of the present invention and the backboard during an emergency situation in which the invention is used.

The head immobilizing straps are preferably constructed similar to the straps associated with the backboard tie-down and the slots for receiving the same. However, in the preferred embodiment the immobilizing straps include a length of material similar in configuration in that it is foam and includes the components of hook and loop material but differs in the sense that an optional buckle is also provided. That is, a buckle having a pair of loops separated by a cross member, or any other suitable buckle configuration such as a simple ring of the appropriate dimension may also be used but enable the ends of the immobilizing strap to pass around and loop around the ring or buckle and reattach itself along its length. That is, the ends of the head immobilizing straps are preferably also one of the above but preferably the opposite component of the hook and loop material than is the elongated body of the strap itself. In this manner, when the end or tab positioned at the end of the strap is looped around the buckle or ring, pulled back and positioned against its longitudinal length, the cooperating component of the tabbed end is opposite the attractive cooperating component of a hook and loop material such that the tab engages and attaches to the length of the strap.

The preferred length of the head immobilizing straps are such that they may pass beneath and lie adjacent the bottom surface of the main board, extend up through immobilizing strap apertures, formed like slots similar to the backboard engaging strap apertures defined above, pass over both of the spaced apart head cushions and attach along their own length. That is, a single strap is inserted up through a pair of spaced apart apertures positioned along the sides of the main board. A length of strap therefore underlies the back surface of the main board and the free ends extend upward through the apertures. The free ends therefore pass through a ring or other buckle configuration and are looped back over onto oneself to provide the hook and loop attachment and semi-rigid engagement of the head cushions to enable the head cushions to maintain their installed positions about the head of a patient to constrain the head and neck of the patient during an emergency situation.

The optional configuration of the apertures themselves may be a complex or a simple notch configuration. The complex configuration incorporates two position portions separated by an extending flange. The position portions are substantially the same width as the width of the head immobilizing strap such that the strap may be positioned in either portion and bounded by the main board and the extending flange. In this manner, at least one or both of the straps may be moved to either position to accommodate the various size features of a particular patient. That is, where someone has a large head and neck or high forehead, it may be desirable to move the uppermost immobilizing strap to its uppermost position to engage the forehead of the patient, whereas a smaller, more slight individual may require the strap to be in its lower position to overlie the forehead.

In addition, the ability to change positions of the head immobilizing straps provides greater flexibility to the user in that if there is significant upper head wound or trauma, the straps may be positioned about the bridge of the nose or upper lip to free the traumatic area from compression and enable the emergency personnel to attend to the site of the wound.

The present invention may, therefore, be summarized in a variety of ways, one of which is the following: ahead immobilizing apparatus for use in conjunction with a backboard, comprising: a substantially rigid mainboard having a top portion, spaced apart sides forming edge portions and a central portion interpositioned therebetween, the mainboard further comprises aperture means positioned along the edge portions of the sides and along the top portion for receiving at least one strap; head pad means removably attached to the mainboard at the central portion for restricting movement of a patient's head; and cooperating attachment means for attaching the head pad means to the mainboard; and immobilizing strap means for immobilizing a patient's head between the head pad means.

The head immobilizing apparatus may further comprise at least one aperture configured to accommodate hardware associated with a patient support surface. The aperture means along the top portion of the mainboard is configured to cooperatively communicate with a handle cutout of a backboard. The aperture means may further comprise at least one pair of opposing apertures each having a notch configuration incorporating a plurality of position portions each separated by an extending flange, and at least one pair of opposing apertures for receiving the backboard engaging strap means.

The cooperating attachment means may further comprise cooperating hook or loop material attached to a bottom surface of the head pad means for attaching the head pad means to the mainboard.

The mainboard is preferably constructed of a corrugated material and configured such that the corrugations extend axially across the mainboard perpendicular to the side edges, and may further include a backboard strap enabling the mainboard to be attached to the backboard The head pad means may further comprise a pair of universally-configured pads, each pad having spaced apart upright side surfaces extending perpendicularly from a bottom and merging at a pair of ends, and a top surface having beveled portions and an ear cutout therebetween. The pads include cutaway portions formed between the ends and either of the upright side surfaces for receiving the immobilizing strap means. The head pad means and the head support means are preferably constructed of open cell foam of a color dissimilar to the color of human blood.

The immobilizing strap means may further comprise a buckle enabling a free end of the immobilizing strap means to be inserted therethrough and folded over to attach to its length. The backboard strap, the immobilizing strap means and the handle strap means comprise a foam-backed cooperating hook and loop material.

It is an object of the present invention to provide a disposable head and neck immobilizer useful in emergency situations.

It is an object of the present invention to provide a disposable head and neck immobilizing apparatus having a main board constructed of a high strength corrugated material.

It is an object of the present invention to provide a head immobilizing apparatus having removable spaced apart head cushions.

It is an object of the present invention to provide a head immobilizing apparatus comprising a plurality of head immobilizing straps which are of sufficient length to be wrapped around the main board and over a pair of head cushions of the present invention to constrain the head cushions and a patient's head between the cushions.

It is an object of the present invention to provide a light weight, strong, disposable head and neck immobilizing apparatus configured to correspond and coincide with the shape of a backboard used by emergency personnel, such as firemen and emergency medical technicians ("EMT's").

It is an object of the present invention to provide a pair of spaced apart head cushions having a minor like configuration such that the head cushions may be used in a left or fight position.

It is an object of the present invention to provide head cushions with a complex surface structure to enable head immobilizing straps to engage the head cushions in a manner such that the contact between the strap and the cushions is maximized for stability.

It is an object of the present invention to provide a main board associated with a disposable head and neck immobilizer with a plurality of apertures to enable the main board to be attached to a backboard used by emergency personnel as well as to provide a means to enable a plurality of head immobilizing straps to immobilize the head of a patient when it is positioned on the main board.

These and other objects, features and advantages shall become apparent after consideration of the scope of the specification and drawings attached hereto. All such objects, features and advantages are contemplated as part of the present invention whose only limitation is the scope of the appended claims.

DETAILED DESCRIPTION OF THE PREFERRED EMBODIMENTS

Figure 1:
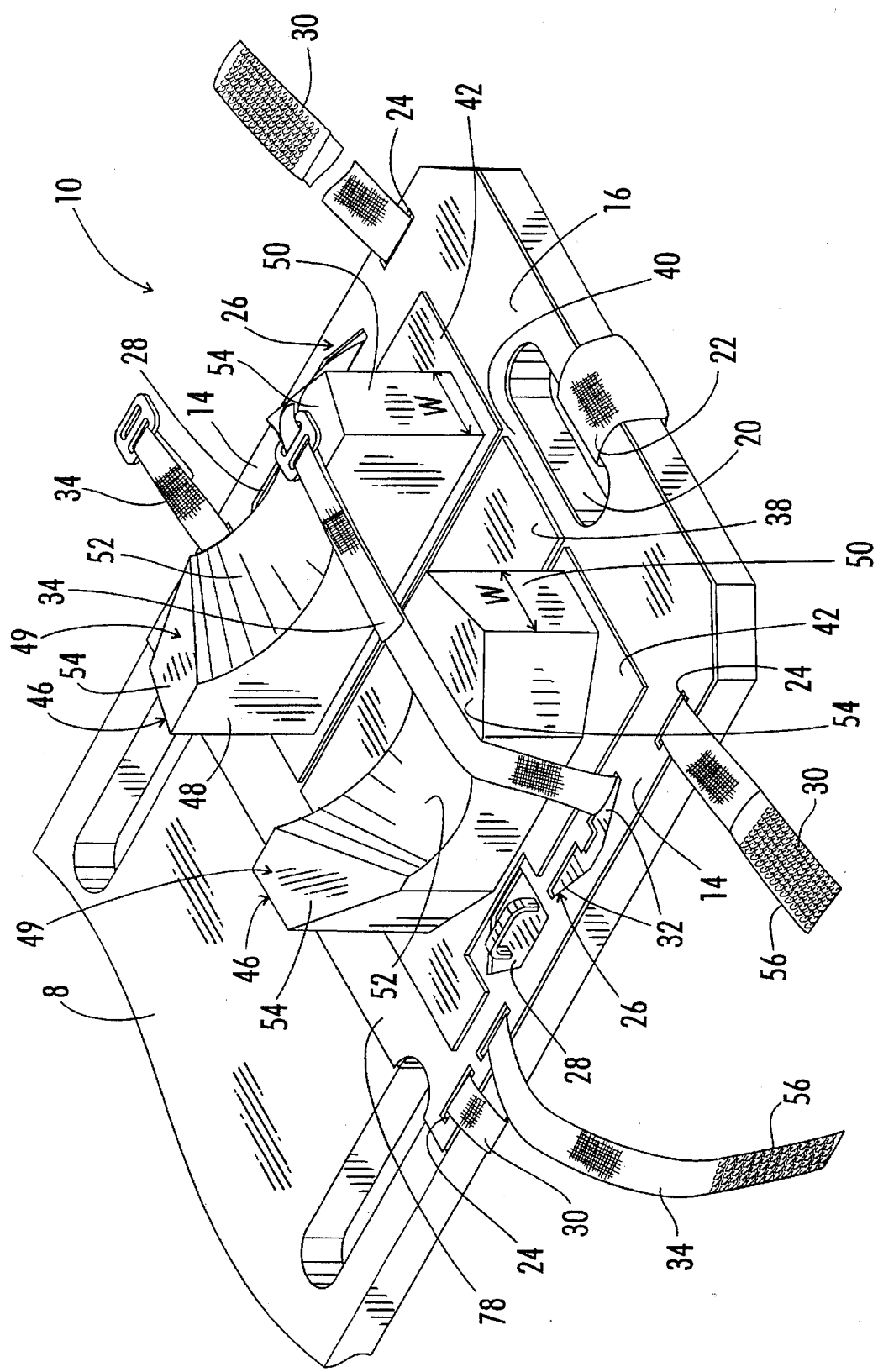
FIG. 1 is an elevated perspective view of an embodiment of the present invention.
Figure 2A:
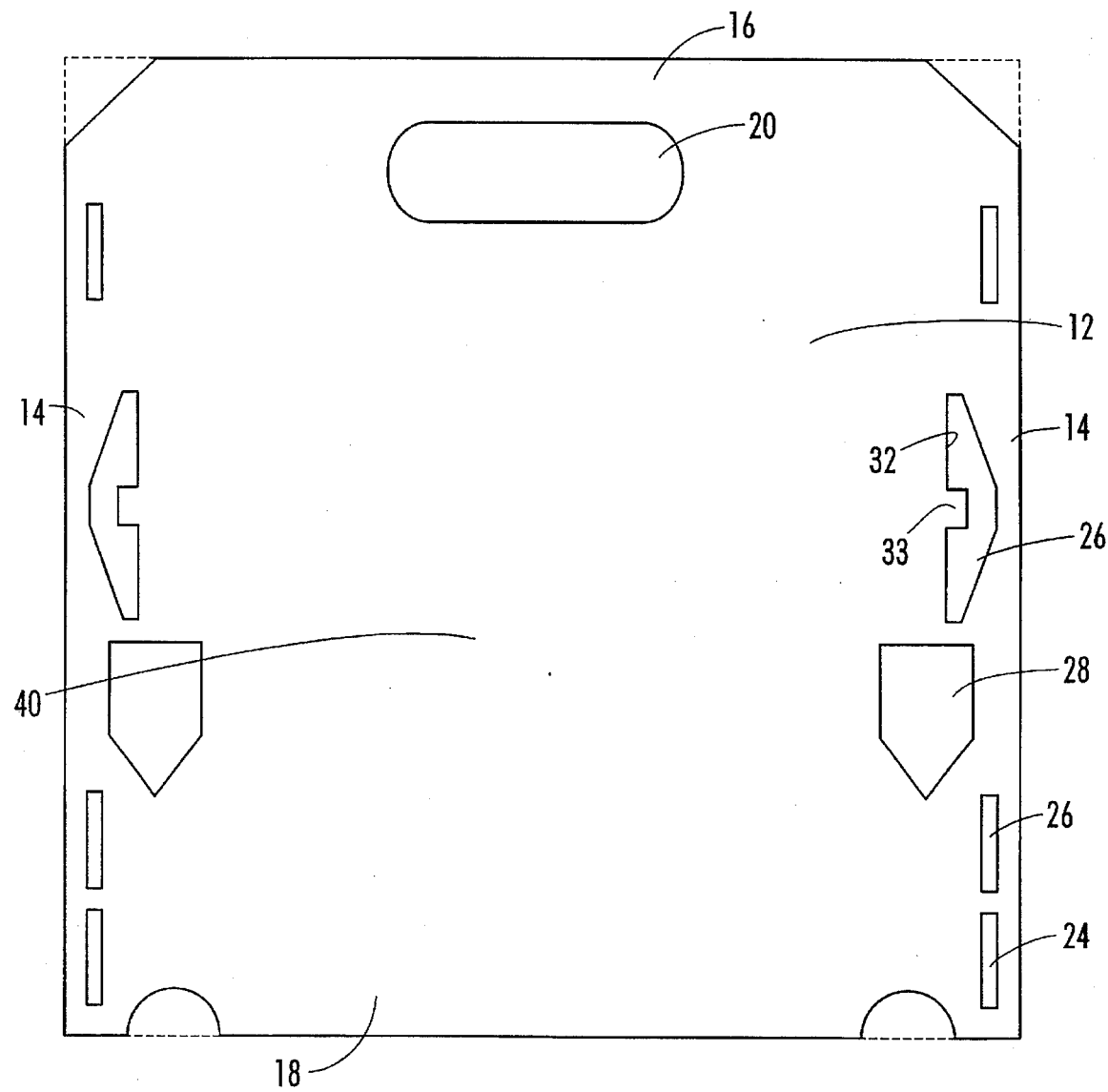
FIG. 2A is an elevated view of an embodiment of the main board of the present invention.
Figure 2B:
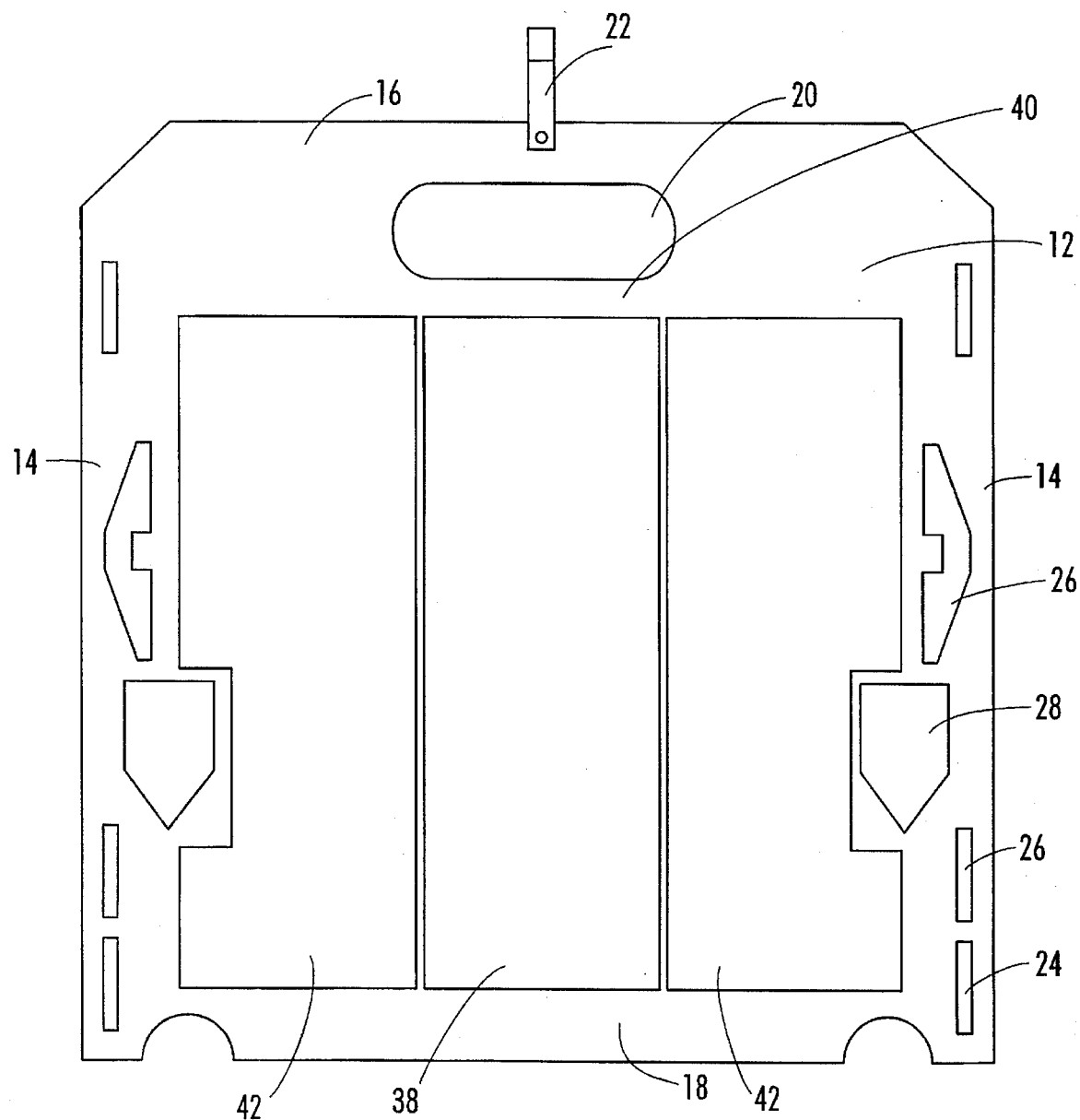
FIG. 2B is an elevated perspective view of an embodiment of the main board shown in FIG. 2A but also further including a head pad pillow and a head cushion attachment sheet.
Figure 3B:
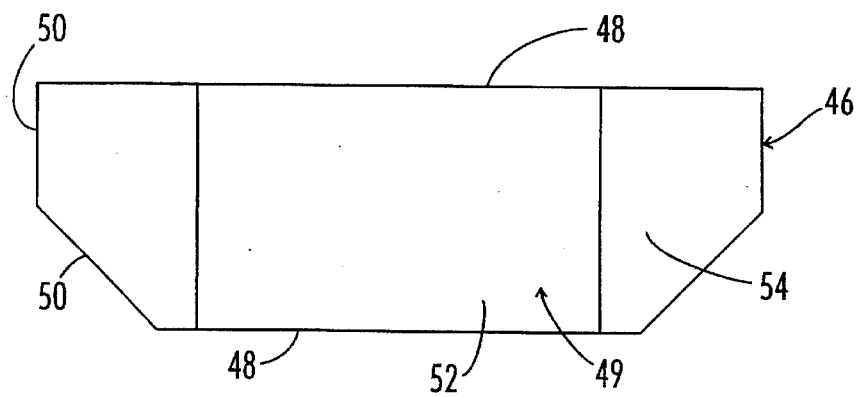
FIG. 3B is a top view of an embodiment of the head cushion shown in FIG. 3A.
Figure 3A:
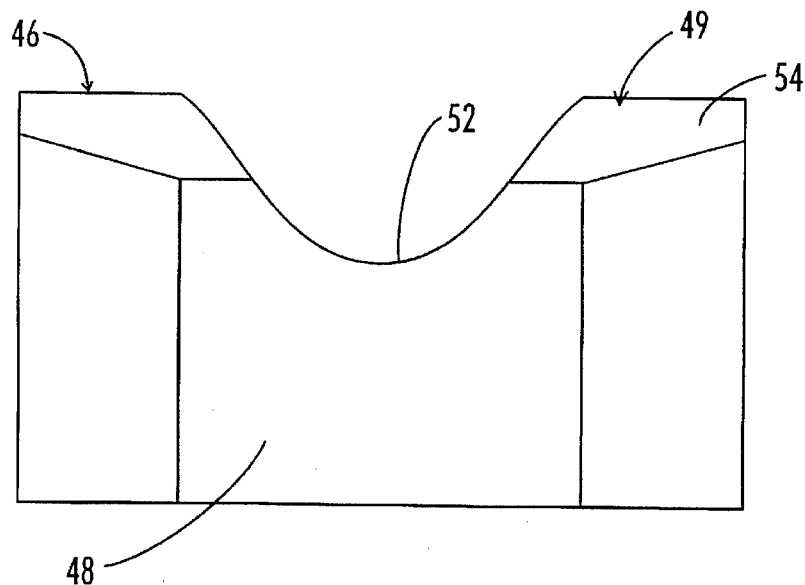
FIG. 3A is a side view of an embodiment of the head cushion of the present invention.
Figure 3C:
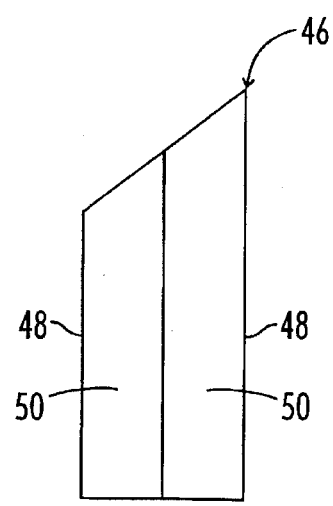
FIG. 3C is an end view of an embodiment of the head cushion shown in FIG. 3A.

With reference to FIG. 1, as well as FIGS. 2A, 2B, 3A–3C, a preferred embodiment of the present invention is designated generally by the reference numeral 10. Preferred embodiment 10 includes a main board 12 having spaced apart sides 14, a top 16, and a bottom portion 18. Associated with the top portion 16 is a handle cutout 20 which receives handle strap 22 such that when the main board 12, configured to correspond to a backboard 8 used in an emergency situation, is positioned on the backboard 8, the handle cutout 20 overlies an opening of the backboard 8 also associated with the handle and the handle strap 22 can be wrapped about the main board 12 and a backboard 8.

With regard to the side portions 14 of the main board, a plurality of slots or strap receiving apertures 24, 26 and 28 are provided. Apertures 24 receive backboard attachment straps 30. The attachment straps are of sufficient length such that they may be looped over and through the aperture 24 and pass beneath the back surface (not shown) of the main board 12 to encircle (not shown) a backboard 8. Apertures 26 may comprise a simple slot configuration like the strap attachment apertures 24 but may also be of a complex configuration. With regard to the complex configured head immobilizing strap apertures, each aperture 26 may further include a strap position portion 32. A central flange or separating flange 33 is interpositioned between the various positions 32 of the adjustable aperture 26. In this manner, a head immobilizing strap 34 may pass through the aperture in any of two locations. It is also contemplated that either or both of the head immobilizing apertures may comprise a single position or a adjustable position having more than one attachment position 32.

Hardware aperture 28 is provided to enable the hardware associated with a backboard 8 to protrude therethrough (not shown). In such embodiment the backboard may contain buckles, loops or other structure such that a tie-down strap or other suitable device may be attached and yet be allowed to pass through the main board 12 to enable such attachment. This is quite common where the backboard includes a pair of attachment posts such that buckling straps can be buckled to the hardware of the backboard and passed over the torso of the patient to secure the patient to the backboard. Of course, in emergency situations, the hardware apertures 28 may also be used as a means to secure the main board to the backboard in the manner described above or enable the immobilizing straps to pass therethrough for a modified form or position of the straps in various situations.

The preferred embodiment of the present invention also includes a head support pad 38 positioned on the central portion 40 of the main board 12. The head support pad or pillow 38 is a substantially rectangular piece of soft cushioned material and is provided as a means to comfort the patient's head when it rests on the main board. Spaced apart from the head support pad are head pad attachment sheets 42. The attachment sheets 42 comprise either the hook or the loop component of a cooperating hook and loop structure. The other of the cooperating hook and loop structure is attached to the bottom 44 of a head pad 46 (See also FIGS. 3A and 3C). Each head pad 46 further includes a pair of spaced apart upright side surfaces 48 extending perpendicularly from the bottom 44. The planar surfaces merge at the ends 50 to provide the width of the head pads 46.

Opposite the bottom surface of each head cushion 46 is a top surface 49 which is generally complex in nature. The top surface 49 includes ear cutouts 52 and beveled portions 54. The ear cutouts are provided such that when a patient's head is interpositioned between a pair of head cushions 46 the ears of the patient may be accessible from the arcuate ear cutouts 52. The beveled portions 54 are provided to enable the mobilizing straps to have greater surface contact with the head cushion to more efficiently constrain the head cushion to the main board 12 as well as keep the head cushions 46 at a predetermined spaced apart relationship to the head of a patient in an emergency situation when the device is used.

Mode of Operation

In use, the attending physician or emergency personnel positions the main board 12 on a backboard 8. The backboard attachment straps 30 are positioned through the slots 24 and the strap is wrapped about the backboard 8 to constrain the main board 12 to it. The immobilizing straps 34 are opened and the head pads 46 are removed from the main board 12. The patient is positioned on the main board with the back of their head resting on the head cushion pillow 38. The attending physician or emergency person repositions the head cushions on both sides of the face to constrain the head in a forward looking position with respect to the main board.

The immobilizing straps 34 already wrapped around the under side of the main board and passed through the immobilizing strap apertures are then fastened to secure the head cushions 46 about the head of the patient. This is accomplished by opening the free ends 56 of the immobilizing straps and inserting them through the opening of the ring or buckle 58 and resecuring the free ends 56 having one component of the cooperating hook and loop material onto itself for attachment. The straps may be changed in position or positioned accurately within the immobilizing strap attachment apertures 26 in any of a variety of positions. Thus, the immobilizing strap may preferably overlie the forehead or where such positioning is ill advised may be moved to overlie another portion of the patient's face for adequate confinement and immobilization.

Once the patient is transported to the emergency health care facility, the immobilizing straps may be removed as can be the head cushions and examined for the collection of blood. In this manner, the blood collecting in the open cell foam of the head cushions can be estimated with respect to quantity to provide the attending physician or emergency personnel with some indication as to blood loss. When the straps are open, the head cushions 46 may then be removed and the patient may be freely lifted or removed from the backboard 8 and main board 12 combination without obstruction. The soiled components of the main board 12, namely, the head cushions 46, may be reattached to the main board 12 and the immobilizing straps 34 fastened to secure the head cushions on the main board or they may be simply laid or strewn over the main board and the entire device removed from the backboard. Upon removal the entire device may be discarded to minimize the possibility of transmission of blood transmitted infectious diseases as well as to eliminate contaminated material from the trauma site.

These and other embodiments and equivalents of the present invention shall become apparent after consideration of the scope of the specification and drawings. All such embodiments and equivalents are contemplated as part of the present invention even though not specifically set forth herein, and whose only limitation is the scope of the appended claims.

What is claimed is:

1. A head immobilizing apparatus for use in conjunction with a backboard, comprising:

a substantially rigid mainboard having a top portion, spaced apart sides forming edge portions and a central portion interpositioned therebetween, the mainboard further comprises aperture means positioned along the edge portions of the sides and along the top portion for receiving at least one strap;

head pad means removably attached to the mainboard at the central portion for restricting movement of a patient's head; and cooperating attachment means for attaching the head pad means to the mainboard;

immobilizing strap means for immobilizing a patient's head between the head pad means; and the aperture means further comprises at least one pair of opposing apertures each having a notch configuration incorporating a plurality of position portions each separated by an extending flange.

2. The head immobilizing apparatus of claim 1 wherein the aperture means further comprises:

at least one aperture configured to accommodate hardware associated with a patient support surface.

3. The head immobilizing apparatus of claim 1 wherein:

the aperture means along the top portion of the mainboard is configured to cooperatively communicate with a handle cutout of a backboard.

4. The head immobilizing apparatus of claim 3, further including:

a backboard strap and a handle strap enabling the mainboard to be attached to the backboard.

5. The head immobilizing apparatus of claim 4 wherein the aperture means further comprises:

at least one pair of opposing apertures for receiving backboard strap.

6. The head immobilizing apparatus of claim 4 wherein the backboard strap, the immobilizing strap means and the handle strap comprises:

a foam-backed cooperating hook and loop material.

7. The head immobilizing apparatus of claim 1 wherein the cooperating attachment means further comprises:

cooperating hook or loop material attached to a bottom surface of the head pad means for attaching the head pad means to the mainboard.

8. The head immobilizing apparatus of claim 1 wherein:

the mainboard is constructed of a corrugated material and configured such that the corrugations extend axially across the mainboard perpendicular to the side edges.

9. The head immobilizing apparatus of claim 1 wherein the head pad means further comprises:

a pair of universally-configured pads, each pad having spaced apart upright side surfaces extending perpendicularly from a bottom and merging at a pair of ends, and a top surface having beveled portions and an ear cutout therebetween.

10. The head immobilizing apparatus of claim 9 wherein:

the pads include cutaway portions formed between the ends and either of the upright side surfaces for receiving the immobilizing strap means.

11. The head immobilizing apparatus of claim 1 wherein the immobilizing strap means further comprises:

a buckle enabling a free end of the immobilizing strap means to be inserted therethrough and folded over to attach to its length.

12. The head immobilizing apparatus of claim 1 wherein:

the head pad means and the head support means are constructed of open cell foam of a color dissimilar to the color of human blood.

* * * * *